United States Patent [19]
Theissen

[11] 3,983,168
[45] Sept. 28, 1976

[54] HALOPHENOXY BENZOIC ACID SALTS

[75] Inventor: Robert J. Theissen, Westfield, N.J.

[73] Assignee: Mobil Oil Corporation, New York, N.Y.

[22] Filed: Sept. 4, 1975

[21] Appl. No.: 610,209

Related U.S. Application Data

[60] Continuation-in-part of Ser. No. 387,829, Aug. 13, 1973, abandoned, which is a continuation-in-part of Ser. No. 334,527, Feb. 22, 1973, abandoned, which is a continuation-in-part of Ser. No. 194,480, Nov. 1, 1971, abandoned, which is a division of Ser. No. 819,412, April 25, 1969, Pat. No. 3,652,645.

[52] U.S. Cl. .................. 260/501.16; 260/520 E; 260/559 R; 71/107; 71/108; 71/111; 71/115; 71/118
[51] Int. Cl.² .................................. C07C 63/33
[58] Field of Search ............... 260/501.16, 520 E; 71/107, 108

[56] References Cited
UNITED STATES PATENTS

| | | |
|---|---|---|
| 3,257,191 | 6/1966 | Weil et al. ........................ 71/107 |
| 3,374,083 | 3/1968 | Loux ................................ 71/108 |
| 3,652,645 | 3/1972 | Theissen ....................... 260/471 R |

FOREIGN PATENTS OR APPLICATIONS

| | | | |
|---|---|---|---|
| 2,019,821 | 11/1970 | Germany | 260/501.16 |
| 6,609,071 | 12/1966 | Netherlands | 260/501.16 |

OTHER PUBLICATIONS

McNew et al., Iowa State Coll. Journal of Science, vol. 24, No. 2, pp. 189–191 (1950).
Lawson, J.A.C.S., 75, 3398–3399 (1953).
Ohyama et al., Chem. Abstracts, vol. 82, 81701(x), (1975).

*Primary Examiner*—James O. Thomas, Jr.
*Assistant Examiner*—G. Breitenstein
*Attorney, Agent, or Firm*—Charles A. Huggett; Hastings S. Trigg

[57] ABSTRACT

Metal salts and amine salts of 2-nitro-5-(halophaenoxy) benzoic acids comprise a class of compounds that are highly effective pre- and post-emergence herbicides.

6 Claims, No Drawings

HALOPHENOXY BENZOIC ACID SALTS

CROSS-REFERENCE TO RELATED APPLICATIONS

This application is a continuation-in-part of copending application Ser. No. 387,829, filed Aug. 13, 1973 (now abandoned), as a continuation-in-part of copending application Ser. No. 334,527, filed Feb. 22, 1973 (now abandoned), as a continuation-in-part of copending application Ser. No. 194,480, filed Nov. 1, 1971 (now abandoned). The last-mentioned application is a division of application Ser. No. 819,412, filed Apr. 25, 1969, now U.S. Pat. No. 3,652,645.

BACKGROUND OF THE INVENTION

Field of the Invention

This invention is concerned with certain phenoxybenzoic acid salts and their use as herbicides.

Description of the Prior Art

It has been proposed to use as herbicides 2-methoxybenzoic acids (U.S. Pat. No. 3,013,054) and 4-phenoxy-benzoic acids (French Pat. No. 1,502,538). It is the discovery of this invention, however, that benzoic acids having a phenoxy substituent in the 5-position are very effective herbicides. U.S. Pat. No. 3,475,427 discloses a position isomer of the acids disclosed herein. This isomeric acid and its salts are ineffective as herbicides.

SUMMARY OF THE INVENTION

This invention provides herbicidal compounds having the formula:

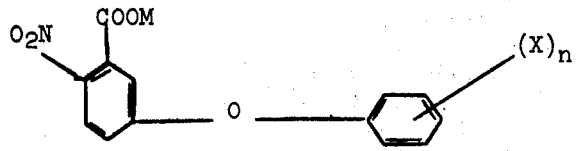

wherein X is halogen, n is 1 to 5, and M is alkali metal (Li, Na, K), alkylammonium ($C_1$–$C_4$) or alkanolammonium ($C_1$–$C_3$).

DESCRIPTION OF SPECIFIC EMBODIMENT

The compounds of this invention are readily prepared by the Ullmann ether synthesis reaction between the alkali metal (Na, K) salt of a halophenol and a 5-halo (Cl, Br)-2-nitrobenzoic acid or an ester, amide, or salt thereof. The 5-halo-2-nitrobenzoic acid is readily prepared by nitrating a m-halotoluene, followed by oxidation of the methyl group by well-known procedures. Generally, the salts of this invention are prepared from the halophenoxybenzoic acid, using well known salt forming procedures.

The salts contemplated herein include metal salts, ammonium salts, and amine salts. The metal salts are the alkali metal salts (Li, Na, K); alkaline earth metal salts (Ca, Mg, Ba, etc.); and transition metal salts (Cu, Fe, etc.).

In addition to the salts of ammonia, the amine salts contemplated include salts of primary amines, secondary amines, tertiary amines, aryl amines, and heterocyclic amines. The primary amines can have 1–30 carbon atoms and can be saturated or unsaturated, straight chain, branched chain, or cyclic. Non-limiting examples of primary amines are methylamine; ethylamine; n-propylamine; isopropylamine; n-butylamine; dodecylamine; triacontylamine; allylamine; 2-propynlamine; cyclohexylamine; propargylamine; isobutylamine; sec-butylamine; 2-ethylhexylamine; cyclopropylmethylamine; t-butylamine; 1,1-dimethyl-2-propynylamine; 1,1-diethyl-2-propynylamine; tallow amine (e.g. Armeen T); 2,2-dimethoxyethylamine; 1-ethynylcyclohexylamine and benzylamine.

The secondary amines can have 2–30 carbon atoms and can be saturated or unsaturated, straight chain, branched chain, or cyclic. Non-limiting examples of secondary amines are dimethylamine, diethylamine, dibutylamine, diotylamine, ditetradecylamine, diallylamine, di-2-hexenylamine, dicyclohexylamine, methylethylamine, methyl cyclohexylamine, diisopropylamine, diisopentylamine, ethyl cyclohexylamine, (3-aminopropyl)alkenylamine wherein the alkenyl group has 16 to 18 carbon atoms; (3-aminopropyl) alkenylamine wherein the alkenyl group has 18, 20 and 22 carbon atoms; and dihydrogenated tallow amine (e.g. Armeen 2HT).

The tertiary amines can have 3–30 carbon atoms and can be saturated or unsaturated, straight chain, branched chain, or cyclic. Non-limiting examples of tertiary amines are trimethylamine, dimethyl ethylamine, triethylamine, tributylamine, trioctylamine, triallylamine, triisopentylamine, tricyclohexylamine, dimethyl octylamine, n-hexadecyldimethylamine (e.g. Armeen DM16D) n-octadecyl-dimethylamine (e.g. Armeen DM18D), methyl di-hydrogenated tallowamine (e.g. Armeen M2HT), and methyl dicocoamine (e.g. Armeen M2C).

Non-limiting examples of arylamines are aniline; 2-chloroaniline; 3-chloroaniline; 4-chloroaniline; 2-methyl-4-chloroaniline; 2,4-dichloroaniline; 3,4-dichloroaniline; 2,6-dichloro-4-nitroaniline; m-trifluoromethylaniline; isopropylaniline; p-methoxyaniline; N-methoxymethyl-2,6-diethylaniline; α-naphthylamine; N-sec-butyl-4-t-butyl-2,6-dinitroaniline; 3-amino-2,5-dichlorobenzoic acid; N,N-dipropyl, α,α,α-trifluoro-2,6-dinitro-p-toluidine; 4-bromo-3-chloroaniline; 4(4'-chlorophenoxy) aniline; $N^3$, $N^3$-diethyl-2,4-dinitro-6-trifluoromethyl-m-phenylenediamine; p-dimethylaminoaniline; diphenylamine; p-bromoaniline; m-aminophenyl-t-butylcarbamate; o-phenylenediamine; m-phenylenediamine; 4-dimethylamino-3,5-dimethylphenol; 4-(methylsulfonyl)-2,6-dinitro-N,N-dipropylaniline; 3,5-dinitro-N,N-dipropylsulfanilamide; N-sec-butyl-4-t-butyl-2,6-dinitroaniline; m-toluidine; p-toluidine; m-t-butylaniline; o-anisidine; p-anisidine; dimethylaniline; o-nitroaniline; p-nitroaniline; and 4,4'-oxydianiline.

Non-limiting examples of heterocyclic amines are 3-amino-1,2,4-triazole; 2-chloro-4-ethylamino-6-isopropylamino-s-triazine; pyridine; piperidine; piperazine; morpholine; 4,4'-dipyridyl; 8-hydroxyquinoline; 4-amino-6-t-butyl-3-(methylthio)-1,2,4-triazine-5(4H)-one; 6-ethoxy-1,2-dihydro-2,2,4-trimethylquinoline; indole; hexahydro-1H-azepine; 4-amino-5-chloro-2-pheyl-3(2H)-pyridazinone; pyrrole; imidazolidine; isoquinoline; 2,4-lutidine; 2-methyl-5-ethylpyridine; 2-dimethyl aminopyridine; α-picoline; β-picoline; γ-picoline; quinoline; and 4,4'-dipyridine.

Non-limiting examples of other salt-forming amino compounds contemplated are 2-chloroethyl dimethylamine; diethanolamine; guanidine; dodecylguanidine; 3-(4-chlorophenyl)-1,1-dimethylurea, 3-(3,4-dichlorophenyl)-1,1-dimethylurea; Fenuron; Tandex;

β-alanine; methyl glycine; glycinamide; aminoacetonitrile; aminoethanthiol; aminoacetic acid; diethyl ethanolamine; diethylenetriamine; isopropanolamine; diisopropanolamine; triisopropanolamine; ethylenediamine; hexamethylenetetramine; hydrazine; phenothiazine; sulfanilic acid; tetraethylenepentamine; thiourea; urea; triethanolamine; triethylenetetramine; diethanol soyaamine (e.g. Ethomeen S-12) and didecaoxyethylene soyaamine (e.g. Ethomeen S-20).

The following example illustrates the preparation of a typical compound of this invention and demonstrates a method for product recovery.

EXAMPLE 1

Methyl 2-nitro-5-(2',4',6'-trichlorophenoxy)benzoate

A stirred solution of methyl 5-chloro-2-nitrobenzoate (17.0 g., 0.079 mole) and the potassium salt of 2,4,6-trichlorophenol (18.6 g., 0.079 mole) in dimethyl sulfoxide (100 ml.) was heated at 90° for 17 hours. The cooled reaction mixture was diluted with water (500 ml.) and then extracted with ether (3 × 100 ml.). The combined ether fractions were washed with 10% sodium hydroxide solution (2 × 30 ml.) and then with a saturated aqueous sodium chloride solution. The ether solution was dried ($Na_2SO_4$) and the solvent evaporated to give a dark oil. Two crystallizations (petroleum ether) gave 1.91 g. of a pale yellow solid, m.p. 101°–103°.

Example 1
I.R. (numol): c=o 1723, c=o 1240, and 1260 $cm^{-1}$;
NMR ($CDCl_3$): methyl 3.91 ppm (3H), quartet;
6.96 ppm (1H, J = 2.5 and 8 c.p.s.), doublet;
7.05 ppm (1H, J = 2.5 c.p.s.), broad singlet;
7.05 ppm (2H), and doublet 8.01 ppm (1H, J = 8 c.p.s.).

EXAMPLES 2 THROUGH 24

The ester of Example 1 was hydrolyzed to the corresponding acid and, using known salt-forming methods, salt compounds within the scope of this invention were prepared.

These compounds are identified below, wherein "A" represents a 2-nitro-5-(2',4'-dichlorophenoxy)benzoate group, "B" represents a 2nitro-5-(2',4',6'-trichlorophenoxy) benzoate group, "C" represents a 2-nitro-5-(2',4'-dichloro-6'-fluorophenoxy)benzoate and "D" represents a 2-nitro-5-(2'-chloro-4'-fluorophenoxy)benzoate:

2. sodium B.
3. ethanolammonium B.
4. dimethylammonium B.
5. potassium A.
6. arachidyl (90%)-behenyl (10%) ammonium A.
7. arachidyl(90%)-behenyl(10%)aminopropylammonium A.
8. arachidyl(90%)-behenyl(10%)ammoniumpropylammonium bis-[A].
9. isobutylammonium A.
10. n-butylammonium A.
11. methoxypropylammonium A.
12. copper bis-[A].
13. 2,2-dimethoxyethylammonium A.
14. t-butylammonium A.
15. benzylammonium A.
16. allylammonium A.
17. diallylammonium A.
18. ethanolammonium A.
19. 3-dimethylaminopropylammonium A.
20. cyclohexylammonium A.
21. di-n-butylammonium A.
22. N,N-dimethyl-3-(4-methyl-3-cyclohexen-1-yl)-butylammonium A.
23. 4-[3-(4-methyl-3-cyclohexen-1-yl)butyl]morpholium A.
24. N,N-dimethyl-3,3-dimethyl-2-norbornylethylammonium A.
29. calcium A.
30. n-propylammonium A.
31. 4(4'-aminophenoxy)anilinium A.
32. 4(4'-phenoxyammonium)anilinium A.
33. 2-propynylammonium A.
34. ammonium A.
35. diethanolammonium A.
36. triethanolammonium A.
37. methylammonium A.
38. trimethylammonium A.
39. isopropylammonium A.
40. sec-butylammonium A.
41. 2-dimethylaminopyridine A.
42. piperidine A.
43. morpholine A.
44. ethylammonium A.
45. diethylammonium A.
46. triethylammonium A.
47. p-methoxyanilinium A.
48. alkenyl($C_{16}$–$C_{18}$)aminopropylammonium A.
49. alkenyl($C_{18}$–$C_{20}$)aminopropylammonium A.
50. o-methoxyanilinium A.
51. m-methoxyanilinium A.
52. m-toluidine A.
53. p-toluidine A.
54. guanidine A.
55. anilinium A.
56. dicyclohexylammonium A.
57. 3,4-dichloroanilinium A.
58. m-chloroanilinium A.
59. p-chloroanilinium A.
60. isopropanolammonium A.
61. diisopropylammonium A.
62. 1,1-dimethyl-2-propynylammonium A.
63. 1,1-diethyl-2-propynylammonium A.
64. 1-ethynylcyclohexylammonium A.
65. n-dodecylamine[a] A. a=Armeen 12D
66. di(hydrogenated tallow)amine[b] A. b=Armeen 2HT
67. n-hexadecyldimethylamine[c] A. c=Armeen DM16D
68. n-octadecyldimethylamine[d] A. d=Armeen DM18D
69. methyl di(hydrogenated tallow)amine[e] A. e=Armeen M2HT
70. methyl di-cocoamine[f] A. f=Armeen M2C
71. diethanol soyaamine[g] A. g=Ethomeen S-12
72. di(decaoxyethylene)soyaamine[h] A. h=Ethomeen S-20
73. 4,4'-dipyridinium A.
74. pyridinium A.
75. triisopropanolammonium A.
76. tallowamine[i] A. i=Armeen T
77. diethanolammonium C.
78. triethanolammonium C.
79. p-methoxyanilinium C.
80. ethanolammonium C.
81. sodium C.
82. ammonium C.

83. cyclohexylammonium C.
84. morpholine C.
85. o-methoxyanilinium C.
86. diethanolammonium B.
87. triethanolammonium B.
88. p-methoxyanilinium B.
89. cyclohexylammonium B.
90. morpholine B.
91. o-methoxyanilinium B.
92. diethanolammonium D.
93. triethanolammonium D.
94. p-methoxyanilinium D.
95. ethanolammonium D.
96. sodium D.
97. ammonium D.
98. cyclohexylammonium D.
99. morpholine D.
100. o-methoxyanilium D.

For comparison, a position isomer of the acids used to form the salts of this invention was prepared, as described in U.S. Pat. No. 3,475,427. Salts of this isomeric acid were prepared by known salt-forming methods. These compounds are:

25. 2-nitro-3-(2',4'-dichlorophenoxy)benzoic acid.
26. ethanolammonium 2-nitro-3-(2',4'-dichlorophenoxy)benzoate.
27. n-propylammonium 2-nitro-3-(2',4'-dichlorophenoxy)benzoate.
28. potassium 2-nitro-3-(2',4'-dichlorophenoxy)benzoate.

The compounds of this invention can be applied in various ways to achieve herbicidal action. They can be applied per se, as solids or in vaporized form, but are preferably applied as the toxic components in pesticidal compositions of the compound and a carrier. These compositions are preferably applied directly to the soil and incorporated therewith. The compositions can be applied, as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, amides and esters, mineral oils such as kerosene, light oils, and medium oils and vegetable oils such as cottonseed oil.

In practice, herbicidal application is measured in terms of pounds of herbicide applied per acre. The compounds of this invention are effective herbicides when applied in herbicidal amounts, i.e., at rates between about 0.2 pounds and about 10 pounds per acre.

HERBICIDAL EFFECTIVENESS

Method of Propagating Test Species

| | |
|---|---|
| Crabgrass | *Digitaria sanquinalis* |
| Yellow foxtail grass | *Setaria glauca* |
| Johnson grass | *Sorgum Halepense* |
| Barnyard grass | *Echinochloa crus-galli* |
| Amaranth pigweed | *Amaranthus retroflexus* |
| Field bindweed | *Convolvulus arvensis* |

-continued

| | |
|---|---|
| Velvet leaf | *Abutilon theophrasti* |
| Turnip | *Brassica sp.* |
| Cotton | *Gossypium hirsutum* var. DPL smooth leaf |
| Corn | *Zea Mays* var. Golden Bantam |
| Bean | *Phaseolus vulgaris* var. Black Valentine |

All crop and weed species are planted individually in 3 inch plastic pots containing potting soil. Four seeds of each of corn, cotton, and snapbeans are seeded to a depth equal to the diameter of the seed. All other species are surface seeded and sprinkled with screened soil in an amount sufficient to cover the seeds. Immediately after planting, all pots are watered by sub-irrigation in greenhouse trays. Pots for the pre-emergence phase are seeded one day before treatment.

Planting dates for the post-emergence phase are varied so that all the seedlings will reach the desired stage of development simultaneously. The proper stage of seedling development for treatment in the post-emergence phase is as follows:

| | |
|---|---|
| GRASSES: | 2 inches in height |
| PIGWEED, BINDWEED, VELVET LEAF & TURNIPS: | 1 or 2 true leaves visible above cotyledons |
| COTTON: | first true leaf 1 inch in length; expanded cotyledons |
| CORN: | 3 inches–4 inches in height |
| BEANS: | primary leaves expanded; growing point at primary leaf node. |

Method of Treatment

Spray applications are made in a hood containing a movable belt and fixed spray nozzle. For passage through the spray hood, one pot of each species (pre-emergence phase) is placed on the forward half of a wooden flat and one pot of established plants (post-emergence phase) is placed on the rear half of the flat. Treatments are moved to the greenhouse after spraying. Watering during the observation period is applied only by subirrigation.

Compounds are screened initially at a rate of application equivalent to four to eight pounds per acre. Two weeks after treatment the pre- and post-emergence percent injury is visually rated. Subsequent testing can be carried out at 2, 1 and 0.5 pounds per acre.

Herbicidal testing of the compounds of Examples 2 through 24 and 30 through 100 and the isomeric compounds showed the results set forth in Table I. The plants are tabulated using the following abbreviations:

| | |
|---|---|
| Crabgrass | CG |
| Yellow foxtail grass | YF |
| Johnson grass | JG |
| Barnyard grass | BG |
| Pigweed | PW |
| Bindweed | BW |
| Velvet leaf | VL |
| Turnip | TP |
| Cotton | CT |
| Corn | CN |
| Bean | BN |

Table 1

| Compound Example No. | Dosage Lbs./Acre | CG | YF | JG | BG | PW | BW | VL | TP | CT | CN | BN |
|---|---|---|---|---|---|---|---|---|---|---|---|---|
| 2 | 8 | 50/80 | –/– | 30/60 | 40/60 | –/– | –/– | –/– | 90/100 | 50/100 | 0/40 | 50/100 |
| 3 | 8 | 20/30 | –/40 | 30/40 | 30/30 | 100/– | –/– | –/– | 90/100 | 50/100 | 0/40 | 80/70 |
|  | 4 | –/– | –/– | –/– | –/– | –/100 | –/– | –/– | –/100 | –/– | –/– | –/– |
|  | 2 | –/– | –/– | –/– | –/– | 100/100 | –/– | –/– | 90/100 | –/– | –/– | –/– |
| 4 | 4 | 0/30 | –/– | 0/40 | 0/– | 0/60 | –/– | –/– | 0/50 | 0/70 | 0/100 | 100/60 |
|  | 4 | 0/100 | –/– | 0/– | 0/– | 0/– | 0/– | 70/– | 90/100 | 0/100 | 0/– | 0/80 |
|  | 2 | 0/10 | –/– | 0/– | 0/– | –/– | 0/– | 40/– | 70/90 | 0/100 | 0/– | 0/40 |
| 5 | 6 | 0/20 | –/– | 0/– | 0/– | –/– | –/– | –/– | 100/100 | 30/100 | 0/– | 30/100 |
|  | 1 | 20/20 | –/– | 0/– | 0/– | –/– | –/– | –/– | 100/90 | 0/20 | 0/– | 0/90 |
| 6 | 2 | 0/0 | –/– | 0/– | 60/– | 100/– | –/– | –/– | 100/100 | 0/90 | 0/– | 0/90 |
|  | 1 | 0/0 | –/– | 0/– | 20/– | –/– | 0/– | 40/– | 80/100 | 20/100 | 0/– | 0/0 |
|  | 0.5 | 0/20 | –/– | 20/– | 0/– | –/– | 50/– | 90/– | 70/90 | 30/70 | 30/– | 0/20 |
| 7 | 2 | 0/0 | –/– | 0/– | 60/– | 100/– | –/– | –/– | 90/100 | 0/80 | 0/– | 0/0 |
|  | 1 | 20/0 | –/– | 90/– | 20/– | –/– | 70/– | 80/– | 70/90 | 0/70 | 30/– | 0/30 |
|  | 0.5 | 30/20 | –/– | 0/– | 30/– | –/– | 60/– | 50/– | 70/80 | 40/50 | 0/– | 0/20 |
| 8 | 2 | 0/0 | –/– | 0/– | 40/– | 100/– | –/– | –/– | 90/90 | 0/30 | 0/– | 0/50 |
|  | 1 | 0/30 | –/– | 0/– | 30/– | –/– | 70/– | 60/– | 90/90 | 50/100 | 0/– | 0/50 |
|  | 0.5 | 20/20 | –/– | 0/– | 0/– | –/– | 50/– | 50/– | 80/100 | 80/90 | 0/– | 30/30 |
| 9 | 2 | 0/0 | –/– | 0/– | 70/– | –/– | 40/– | 100/– | 100/100 | 40/90 | 0/– | 0/90 |
| 10 | 2 | 20/20 | –/– | 0/– | 50/– | –/– | 90/– | 100/– | 100/80 | 100/100 | 20/– | 0/50 |
| 11 | 2 | 20/0 | –/– | 40/– | 50/– | –/– | 100/– | 100/– | 100/100 | 100/100 | 0/– | 20/70 |
| 12 | 10 | 0/20 | –/– | 0/– | 0/– | 90/– | –/– | –/– | 100/90 | 40/30 | 20/– | –/– |
| 13 | 2 | 0/0 | –/– | 50/– | 50/– | –/– | 90/– | 20/– | 100/90 | 30/100 | 0/– | 0/– |
| 14 | 2 | 20/0 | –/– | 40/– | 20/– | –/– | 30/– | 20/– | 100/90 | 0/100 | 30/0 | 0/– |
| 15 | 2 | 0/0 | –/– | 0/– | 30/– | –/– | 40/– | 20/– | 100/100 | 50/100 | 0/– | 0/– |
| 16 | 2 | 30/0 | –/– | 0/– | 20/– | –/– | 80/– | 20/– | 100/70 | 100/100 | 0/– | 0/– |
| 17 | 2 | 0/20 | –/– | 50/– | 30/– | –/– | 90/– | 20/– | 80/80 | 30/100 | 0/– | 0/– |
| 18 | 2 | 30/20 | –/– | 0/– | 0/– | –/– | 30/– | 20/– | 90/100 | 100/100 | 0/– | 0/– |
| 19 | 2 | 20/0 | –/– | 70/– | 20/– | –/– | 50/– | 20/– | 100/100 | 0/40 | 0/– | 20/– |
| 20 | 2 | 0/0 | –/– | 40/– | 0/– | –/– | 60/– | 30/– | 100/80 | 0/100 | 20/– | 0/– |
| 21 | 2 | 0/0 | –/– | 30/– | 20/– | –/– | 50/– | 20/– | 100/100 | 50/100 | 0/– | 0/– |
| 22 | 2 | 0/0 | –/– | 40/– | 0/– | –/– | 80/– | 30/– | 90/100 | 0/100 | 0/– | 0/– |
| 23 | 2 | 0/20 | –/– | 30/– | 0/– | –/– | 70/– | 20/– | 60/60 | 0/20 | 0/– | 0/– |
| 24 | 2 | 0/0 | –/– | 20/– | 0/– | –/– | 70/– | 20/– | 60/90 | 0/100 | 20/– | 0/– |
| 25 | 4 | 0/0 | –/– | 0/– | 30/– | –/– | 20/– | 0/– | 0/0 | 0/0 | 0/– | 0/0 |
| 26 | 4 | 0/0 | –/– | 0/– | 0/– | –/– | 0/– | 0/– | 0/0 | 0/0 | 20/– | 0/0 |
| 27 | 4 | 0/0 | –/– | 20/– | 0/– | –/– | 0/– | 0/– | 0/0 | 0/0 | 0/– | 0/0 |
| 28 | 4 | 40/0 | –/– | 0/– | 60/– | –/– | 20/– | 0/– | 0/20 | 0/0 | 0/– | 0/0 |
| 29 | 10 | 10/10 | –/– | 10/– | 10/– | –/– | 100/– | 80/– | 0/0 | 20/0 | 20/– | 0/0 |
| 30 | 2 | 0/0 | –/– | 0/– | 0/– | –/– | 100/– | 40/– | 100/100 | 10/70 | 10/– | 10/60 |
| 31 | 2 | 0/0 | –/– | 0/– | 0/– | –/– | 30/– | 50/– | 90/90 | 0/100 | 0/– | 30/0 |
| 32 | 2 | 0/0 | –/– | 0/– | 0/– | –/– | 40/– | 70/– | 100/80 | 90/40 | 0/– | 0/0 |
| 33 | 2 | 0/0 | –/– | 0/– | 0/– | –/– | 30/– | 90/– | 90/90 | 30/40 | 0/– | 0/0 |
| 34 | 2 | 0/0 | –/– | 0/– | 0/– | –/– | 0/– | 80/– | 100/– | 0/30 | 0/– | 0/20 |
| 35 | 1 | 0/20 | –/– | 0/– | 0/– | –/– | 0/– | 40/– | 90/100 | 0/60 | 0/– | 0/100 |
| 36 | 1 | 0/0 | –/– | 0/– | 0/– | –/– | 0/– | 30/– | 70/90 | 0/70 | 0/– | 0/100 |
| 37 | 1 | 0/0 | –/– | 20/– | 0/– | –/– | 40/– | 60/– | 60/90 | 0/60 | 0/– | 0/100 |
| 38 | 1 | 0/0 | –/– | 0/– | 0/– | –/– | 0/– | 50/– | 70/90 | 0/100 | 0/– | 0/100 |
| 39 | 1 | 0/0 | –/– | 0/– | 0/– | –/– | 50/– | 30/– | 70/90 | 0/90 | 30/– | 0/100 |
| 40 | 1 | 0/30 | –/– | 0/– | 0/– | –/– | 0/– | 30/– | 70/100 | 0/100 | 0/– | 0/100 |
| 41 | 1 | 0/30 | –/– | 0/– | 0/– | –/– | 50/– | 80/– | 80/100 | 0/100 | 0/– | 0/100 |
| 42 | 2 | 20/0 | –/– | 0/– | 0/– | –/– | 50/– | 80/– | 90/100 | 0/100 | 0/– | 0/100 |
| 43 | 2 | 0/0 | –/– | 0/– | 0/– | –/– | 60/– | 80/– | 90/100 | 0/100 | 0/– | 0/100 |
| 44 | 1 | 0/0 | –/– | 0/– | 0/– | –/– | 0/– | 90/– | 90/90 | 0/90 | 30/– | 0/90 |
| 45 | 1 | 0/0 | –/– | 0/– | 0/– | –/– | 0/– | 60/– | 80/100 | 0/100 | 0/– | 0/100 |
| 46 | 1 | 0/0 | –/– | 0/– | 0/– | –/– | 0/– | 50/– | 70/90 | 20/100 | 0/– | 0/100 |
| 47 | 1 | 0/0 | –/– | 0/– | 0/– | –/– | 40/– | 60/– | 90/90 | 0/100 | 0/– | 0/100 |
| 48 | 1 | 0/0 | –/– | 0/– | 0/– | –/– | 0/– | 60/– | 90/90 | 0/20 | 20/– | 0/30 |
| 49 | 1 | 0/0 | –/– | 0/– | 0/– | –/– | 0/– | 60/– | 70/90 | 0/40 | 0/– | 0/0 |
| 50 | 1 | 0/0 | –/– | 0/– | 0/– | –/– | 0/– | 50/– | 50/100 | 0/40 | 0/– | 0/70 |
| 51 | 1 | 0/0 | –/– | 0/– | 0/– | –/– | 80/– | 90/– | 100/90 | 0/100 | 0/– | 0/100 |
| 52 | 1 | 0/0 | –/– | 0/– | 0/– | –/– | 80/– | 80/– | 90/90 | 0/90 | 0/– | 0/90 |
| 53 | 1 | 0/0 | –/– | 0/– | 0/– | –/– | 50/– | 80/– | 100/90 | 30/90 | 40/– | 0/90 |
| 54 | 1 | 0/0 | –/– | 0/– | 0/– | –/– | 30/– | 80/– | 90/90 | 0/90 | 0/– | 0/90 |
| 55 | 1 | 0/0 | –/– | 0/– | 0/– | –/– | 0/– | 30/– | 70/90 | 0/20 | 30/– | 0/20 |
| 56 | 1 | 40/0 | –/– | 0/– | 0/– | –/– | 0/– | 60/– | 90/90 | 20/20 | 30/– | 0/30 |
| 57 | 1 | 0/0 | –/– | 0/– | 0/– | –/– | 0/– | 40/– | 90/70 | 0/80 | 0/– | 0/40 |
| 58 | 1 | 0/0 | –/– | 0/– | 0/– | –/– | 50/– | 80/– | 100/90 | 0/90 | 30/– | 0/100 |
| 59 | 1 | 0/0 | –/– | 0/– | 0/– | –/– | 100/– | 80/– | 90/90 | 30/100 | 0/– | 0/100 |
| 60 | 1 | 0/0 | –/– | 0/– | 0/– | –/– | 90/– | 90/– | 90/70 | 0/90 | 0/– | 0/30 |
| 61 | 1 | 0/0 | –/– | 0/– | 0/– | –/– | 50/– | 60/– | 80/100 | 0/90 | 0/– | 0/100 |
| 62 | 1 | 0/0 | –/– | 0/– | 0/– | –/– | 30/– | 0/– | 100/90 | 0/90 | 0/– | 0/100 |
| 63 | 1 | 0/0 | –/– | 0/– | 0/– | –/– | 0/– | 60/– | 90/90 | 0/50 | 0/– | 0/90 |
| 64 | 1 | 0/0 | –/– | 0/– | 0/– | –/– | 0/– | 50/– | 80/90 | 0/20 | 0/– | 0/100 |
| 65 | 1 | 0/0 | –/– | 20/– | 0/– | –/– | 30/– | 50/– | 90/90 | 20/40 | 0/– | 0/100 |
| 66 | 1 | 0/0 | –/– | 0/– | 0/– | –/– | 40/– | 50/– | 90/90 | 50/60 | 0/– | 0/50 |
| 67 | 1 | 0/30 | –/– | 0/– | 0/– | –/– | 0/– | 0/– | 20/50 | 40/– | 0/– | 0/0 |
| 68 | 1 | 0/0 | –/– | 0/– | 0/– | –/– | 0/– | 30/– | 90/90 | 20/50 | 0/– | 0/100 |
| 69 | 1 | 0/0 | –/– | 0/– | 0/– | –/– | 0/– | 60/– | 70/90 | 0/30 | 0/– | 0/90 |
| 70 | 1 | 0/0 | –/– | 0/– | 0/– | –/– | 0– | 30/– | 70/90 | 0/90 | 30/– | 0/100 |
| 71 | 1 | 0/0 | –/– | 0/– | 0/– | –/– | 30/– | 50/– | 70/90 | 0/90 | 0/– | 0/100 |
| 72 | 1 | 0/0 | –/– | 0/– | 0/– | –/– | 40/– | 40/– | 60/90 | 0/60 | 0/– | 0/100 |
| 73 | 1 | 0/0 | –/– | 0/– | 0/– | –/– | 0/– | 30/– | 50/90 | 0/50 | 0/– | 0/100 |
| 74 | 1 | 0/0 | –/– | 0/– | 0/– | –/– | 0/– | 50/– | 90/90 | 0/90 | 0/– | 0/90 |
| 75 | 1 | 0/0 | –/– | 0/– | 0/– | –/– | 0/– | 80/– | 90/90 | 30/70 | 0/– | 0/100 |
| 76 | 1 | 0/0 | –/– | 0/– | 0/– | –/– | 0/– | 40/– | 40/100 | 0/90 | 0/– | 0/100 |
| 77 | 1 | 0/20 | –/– | 0/– | 0/– | –/– | 50/– | 50/– | 60/100 | 30/80 | 0/– | 0/100 |
| 78 | 1 | 0/20 | –/– | 20/– | 0/– | –/– | 20/– | 50/– | 90/100 | 20/40 | 0/– | 0/40 |
| 79 | 1 | 0/0 | –/– | 0/– | 0/– | –/– | 30/– | 80/– | 90/100 | 0/90 | 0/– | 0/0 |

Table 1-continued

| Compound Example No. | Dosage Lbs./Acre | CG | YF | JG | BG | PW | Pre-/Post-Emergence BW | VL | TP | CT | CN | BN |
|---|---|---|---|---|---|---|---|---|---|---|---|---|
| 80 | 1 | 0/0 | -/- | 0/- | 0/- | -/- | 0/- | 90/- | 90/90 | 0/100 | 0/- | 0/50 |
| 81 | 1 | 0/30 | -/- | 0/- | 0/- | -/- | 20/- | 70/- | 80/90 | 0/100 | 0/- | 0/30 |
| 82 | 1 | 0/- | -/- | 0/- | 0/- | -/- | 20/- | 90/- | 90/- | 0/- | 0/- | 0/- |
| 83 | 1 | 30/20 | -/- | 20/- | 0/- | -/- | 100/- | 70/- | 100/100 | 20/100 | 0/- | 0/30 |
| 84 | 1 | 0/20 | -/- | 0/- | 0/- | -/- | 50/- | 100/- | 100/100 | 20/50 | 0/- | 0/50 |
| 85 | 1 | 0/0 | -/- | 0/- | 0/- | -/- | 60/- | 90/- | 100/100 | 0/40 | 0/- | 0/30 |
| 86 | 1 | 0/0 | -/- | 0/- | 0/- | -/- | 0/- | 20/- | 90/80 | 0/20 | 0/- | 0/0 |
| 87 | 1 | 0/0 | -/- | 0/- | 0/- | -/- | 0/- | 30/- | 80/80 | 0/20 | 0/- | 0/0 |
| 88 | 1 | 0/0 | -/- | 0/- | 0/- | -/- | 0/- | 60/- | 80/20 | 20/20 | 0/- | 20/- |
| 89 | 1 | 0/0 | -/- | 0/- | 0/- | -/- | 0/- | 20/- | 60/100 | 0/30 | 0/- | 0/40 |
| 90 | 1 | 0/0 | -/- | 0/- | 0/- | -/- | 20/- | 80/- | 100/90 | 20/30 | 30/- | 0/40 |
| 91 | 1 | 0/0 | -/- | 0/- | 0/- | -/- | 40/- | 70/- | 90/90 | 0/30 | 0/- | 0/20 |
| 92 | 1 | 0/0 | -/- | 0/- | 0/- | -/- | 0/- | 30/- | 30/50 | 0/0 | 0/- | 0/90 |
| 93 | 1 | 0/20 | -/- | 0/- | 0/- | -/- | 0/- | 30/- | 0/60 | 0/0 | 0/- | 0/80 |
| 94 | 1 | 0/20 | -/- | 0/- | 0/- | -/- | 0/- | 30/- | 20/90 | 0/60 | 0/- | 0/100 |
| 95 | 1 | 0/0 | -/- | 0/- | 0/- | -/- | 0/- | 80/- | 70/60 | 0/90 | 0/- | 0/90 |
| 96 | 1 | 0/0 | -/- | 0/- | 0/- | -/- | 0/- | 60/- | 60/50 | 0/40 | 0/- | 0/80 |
| 97 | 1 | 0/0 | -/- | 20/- | 0/- | -/- | 0/- | 40/- | 60/40 | 0/30 | 0/- | 0/90 |
| 98 | 1 | 0/0 | -/- | 0/- | 0/- | -/- | 0/- | 40/- | 40/70 | 20/90 | 0/- | 0/60 |
| 99 | 1 | 0/0 | -/- | 0/- | 0/- | -/- | 0/- | 70/- | 90/70 | 0/100 | 0/- | 0/100 |
| 100 | 1 | 0/0 | -/- | 0/- | 0/- | -/- | 30/- | 70/- | 80/80 | 0/80 | 0/- | 0/100 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A compound having the formula:

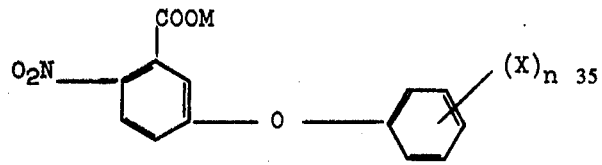

wherein X is halogen, $n$ is 1 to 5, and M is alkali metal (Li, Na, K), alkylammonium ($C_1$–$C_4$), or alkanolammonium ($C_1$–$C_3$).

2. A compound of claim 1, wherein M is sodium.
3. A compound of claim 1, wherein M is potassium.
4. A compound of claim 1, wherein M is ethylammonium.
5. A compound of claim 1, wherein M is ethanolammonium.
6. A compound of claim 1, wherein M is $C_4$ alkylammonium.

* * * * *